US010654885B2

(12) United States Patent
Lenna et al.

(10) Patent No.: US 10,654,885 B2
(45) Date of Patent: May 19, 2020

(54) PROCESS FOR THE PREPARATION OF 9 BETA,10 ALPHA-PROGESTERONE (RETROPROGESTERONE)

(71) Applicant: INDUSTRIALE CHIMICA S.R.L., Milan (IT)

(72) Inventors: Roberto Lenna, S. Giorgio Su Legnano (IT); Claudio Delfrate, Rho (IT); Davide Rigamonti, Lambrugo (IT)

(73) Assignee: INDUSTRIALE CHIMCA S.R.L., Milan (IT)

( * ) Notice: Subject to any disclaimer, the term of this patent is extended or adjusted under 35 U.S.C. 154(b) by 0 days.

(21) Appl. No.: 16/479,160

(22) PCT Filed: Jan. 18, 2018

(86) PCT No.: PCT/EP2018/051147
§ 371 (c)(1),
(2) Date: Jul. 18, 2019

(87) PCT Pub. No.: WO2018/134278
PCT Pub. Date: Jul. 26, 2018

(65) Prior Publication Data
US 2020/0040029 A1 Feb. 6, 2020

(30) Foreign Application Priority Data
Jan. 18, 2017 (IT) .................. 102017000004904

(51) Int. Cl.
C07J 15/00 (2006.01)
C07J 75/00 (2006.01)

(52) U.S. Cl.
CPC ............. C07J 15/005 (2013.01); C07J 75/00 (2013.01)

(58) Field of Classification Search
CPC ................... C07J 15/005; C07J 75/00
See application file for complete search history.

(56) References Cited

U.S. PATENT DOCUMENTS 3,496,199 A * 2/1970 Uskovic ................... C07J 75/00
552/603
3,766,213 A * 10/1973 Furst et al. .......... C07C 59/205
549/279

FOREIGN PATENT DOCUMENTS

WO 2016/044558 A1 3/2016

OTHER PUBLICATIONS

International Search Report and Written Opinion for corresponding Application No. PCT/EP2018/051147 (dated May 2, 2018).

* cited by examiner

Primary Examiner — Paul A Zucker
(74) Attorney, Agent, or Firm — Pepper Hamilton LLP

(57) ABSTRACT

The present invention refers to a new process for the synthesis of (9β,10α)-pregn-4-ene-3,20-dione, commonly known as retroprogesterone, having the formula (1) shown below.

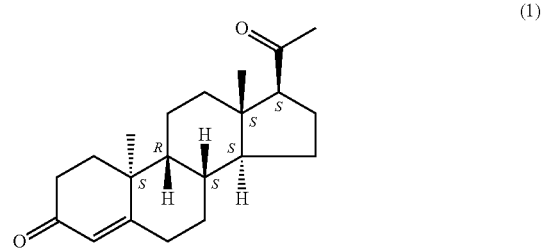

5 Claims, No Drawings

PROCESS FOR THE PREPARATION OF 9 BETA,10 ALPHA-PROGESTERONE (RETROPROGESTERONE)

This application is a national stage application under 35 U.S.C. § 371 of PCT Application No. PCT/EP2018/051147, filed Jan. 18, 2018, which claims the priority benefit of Italy Patent Application No. 102017000004904, filed Jan. 18, 2017.

FIELD OF THE INVENTION

The present invention refers to the field of processes for the synthesis of active ingredients for pharmaceutical use, and in particular to a process for the industrial scale preparation of 9β,10α-progesterone, also known as retroprogesterone.

STATE OF THE ART

Retroprogesterones are a class of steroids having hormonal activity which are used in the cure and treatment of dysfunctions of the female reproductive apparatus and of pregnancy.

The parent compound of the family is retroprogesterone, a compound having the 4-ring steroid structure, as shown in the following figure:

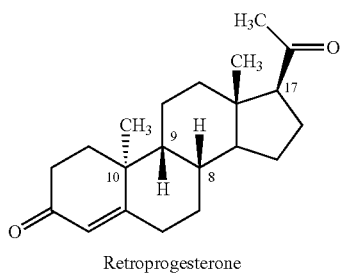

Retroprogesterone wherein the spatial orientation of the hydrogen atoms in positions 8 and 9 is β, while that of methyl in position 10 is α; this structure is different from that of progesterone, having the so called "natural" configuration shown in the following figure, with the opposite orientation of the hydrogen atom in position 9 (α) and of the methyl in position 10 (β).

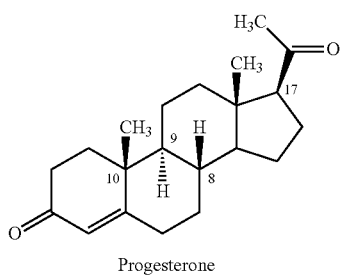

Progesterone

The four rings making up the basic steroid skeleton are indicated in the field with the letters A to D, as shown in the following figure:

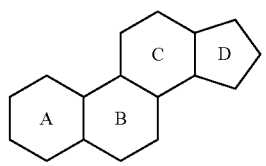

Retroprogesterones useful for therapeutic uses are, for example, dydrogesterone and trengestone having the following structural formulae:

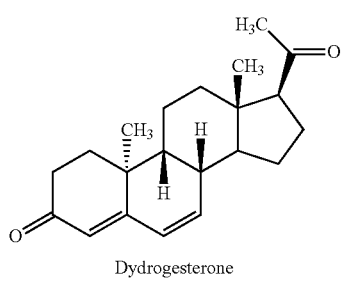

Dydrogesterone

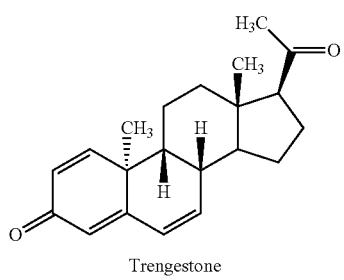

Trengestone

Dydrogesterone has been shown to be effective in the treatment of various conditions associated with a lack of progesterone, including infertility caused by luteal insufficiency, spontaneous abortion (threatened or recurrent), menstrual disorders, premenstrual syndrome, and endometriosis, while trengestone has been used for the treatment of problems related to the menstrual cycle.

The compound of formula (1) shown below, having the chemical name 17β-hydroxy-des-A-androst-9,10-en-5-one, is a useful intermediate in the synthesis of retroprogesterones:

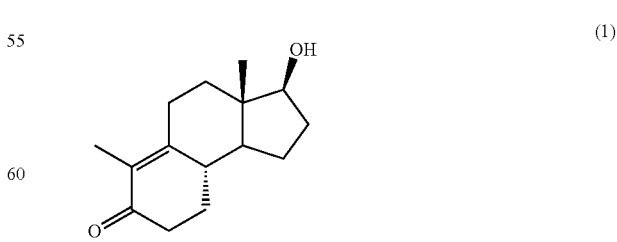

This compound is described in various publications, including J. Org. Chem, 32, 3008 (1967) and the PCT Patent Application WO 2017/072719 A1 filed 28 Oct. 2016.

Compound (I) is obtained from the hydrogenation of (1):

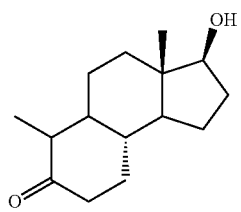
(I)

whose use in the synthesis of retroprogesterone is described in Journal of Organic Chemistry, Vol 33, No 9, September 1968, pages 3548-51.

The key reaction in this process is the creation of the A ring of the steroid skeleton by anellation of the intermediate (V) with methyl vinyl ketone (MVK) to yield retroprogesterone (VI), as shown in the following scheme:

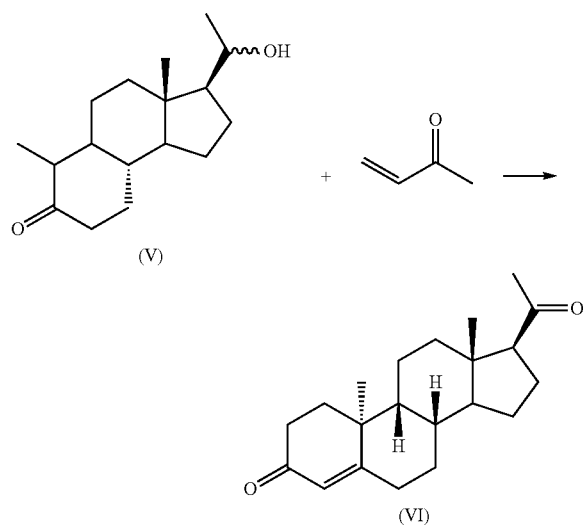

This process scheme therefore follows the sequence:

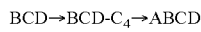

which shows that the steroid of interest (ABCD) is obtained from the reaction between an intermediate comprising the B, C and D rings and a reagent with four carbon atoms.

In the synthetic route described in the article above, starting from 2.64 g of compound (V), after the reaction, by chromatography are obtained 1.16 g of intermediate (V) and 380 mg of annulated product (VI) which is then oxidized using Cr(VI) in acetone, to obtain 124 mg of pure retroprogesterone after purifications.

The yield of the reaction is very low, less than 4% by moles. It is therefore apparent that this synthetic procedure has only an academic interest, and it is without practical applicability for a large-scale production having the synthesis of an API as its final objective.

The same sequence of reactions (cyclization and oxidation) described in the same article to obtain retroprogesterone have similar criticalities as those described above for retroprogesterone.

The indication from the article cited above is of a process, which is useful for the preparation of a sample for analytical use, but without applicability as an industrial process.

The object of the present invention is to provide a simpler synthetic route for the preparation of Retroprogesterone (VI) compared to the processes described in the prior art, and with an industrial applicability.

SUMMARY OF THE INVENTION

This and other objects are achieved by the present invention, which relates to a process for the synthesis of Retroprogesterone, compound (VI), comprising the following steps:

a) reaction of compound (7), (3S,3aS,5aR,6R,9aR,9bS)-3-((S)-1-hydroxyethyl)-3a,6-dimethyldodecahydro-7H-cyclopenta[a]naphthalen-7-one, with acrylonitrile to yield compound (6) 3-((3S,3aS,5aR,6S,9aS,9bS)-3-((S)-1-hydroxyethyl)-3a,6-dimethyl-7-oxododecahydro-1H-cyclopenta[a]naphthalen-6-yl)propanenitrile:

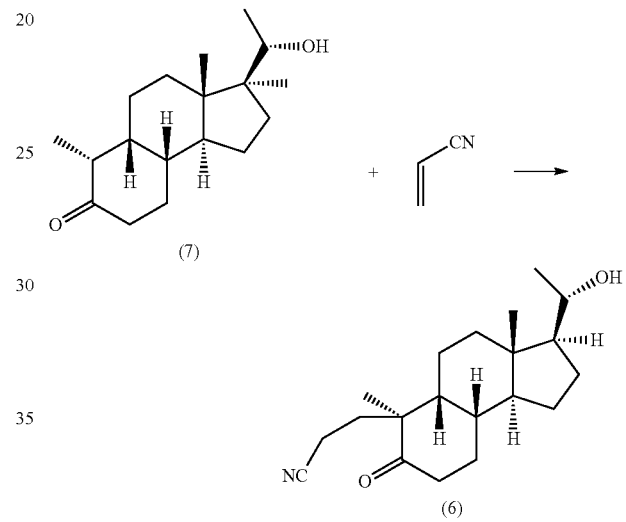

b) reaction of compound (6) with a strong base to yield compound (5), 3-((3S,3aS,5aR,6S,9aS,9bS)-3-((S)-1-hydroxyethyl)-3a,6-dimethyl-7-oxododecahydro-1H-cyclopenta[a]naphthalen-6-yl)propanoic acid:

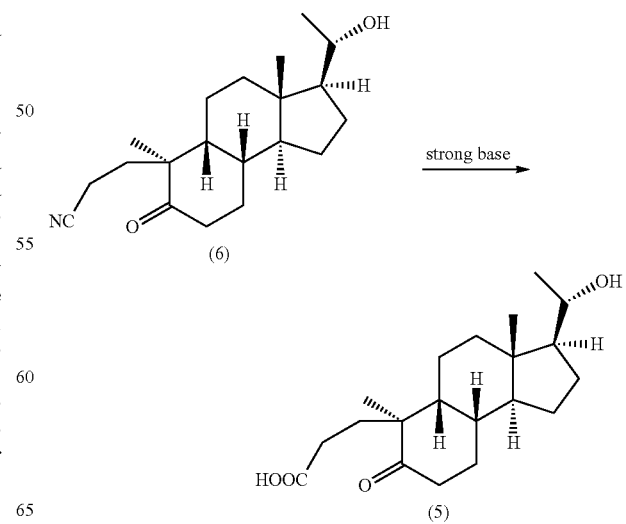

c) reaction of compound (5) with acetic anhydride to yield compound (4), (S)-1-((4aS,4bR,6aS,7S,9aS,9bS)-4a,6a-dimethyl-2-oxo-2,3,4,4a,4b,5,6,6a,7,8,9,9a,9b,10-tetradecahydroindeno[5,4-f]chromen-7-yl)ethyl acetate:

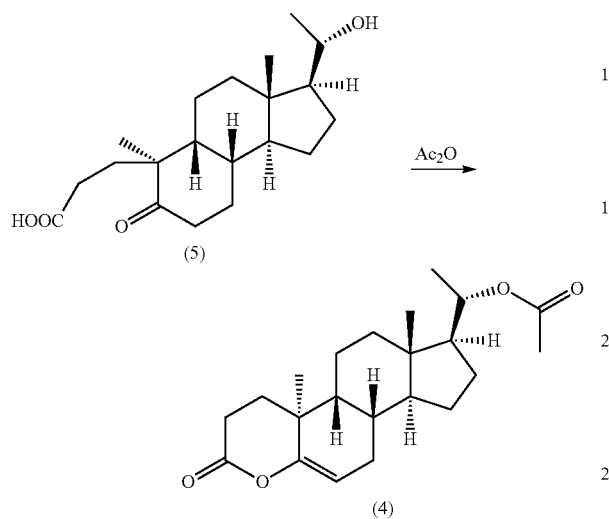

d) reaction of compound (4) with a $C_1$ organometallic reagent to yield compound (3), (S)-1-((3S,3aS,5aR,6S,9aS,9bS)-3a,6-dimethyl-7-oxo-6-(3-oxobutyl)dodecahydro-1H-cyclopenta[a]naphthalen-3-yl)ethyl acetate:

wherein by "$C_1$ organometallic reagent" is meant an organometallic compound in which the organic moiety comprises only one carbon atom;

e) reaction of compound (3) with a strong base to yield compound (2), (8S,9R,10S,13S,14S,17S)-17-((S)-1-hydroxyethyl)-10,13-dimethyl-1,2,6,7,8,9,10,11,12,13,14,15,16,17-tetradecahydro-3H-cyclopenta[a]phenanthren-3-one:

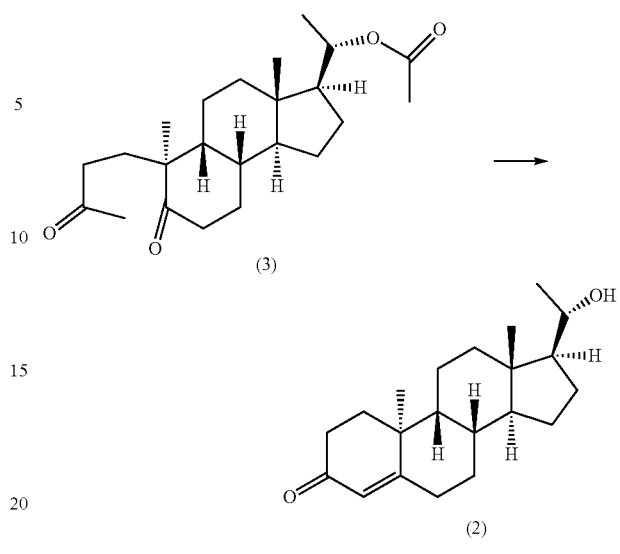

f) oxidation of intermediate (2) to obtain Retroprogesterone:

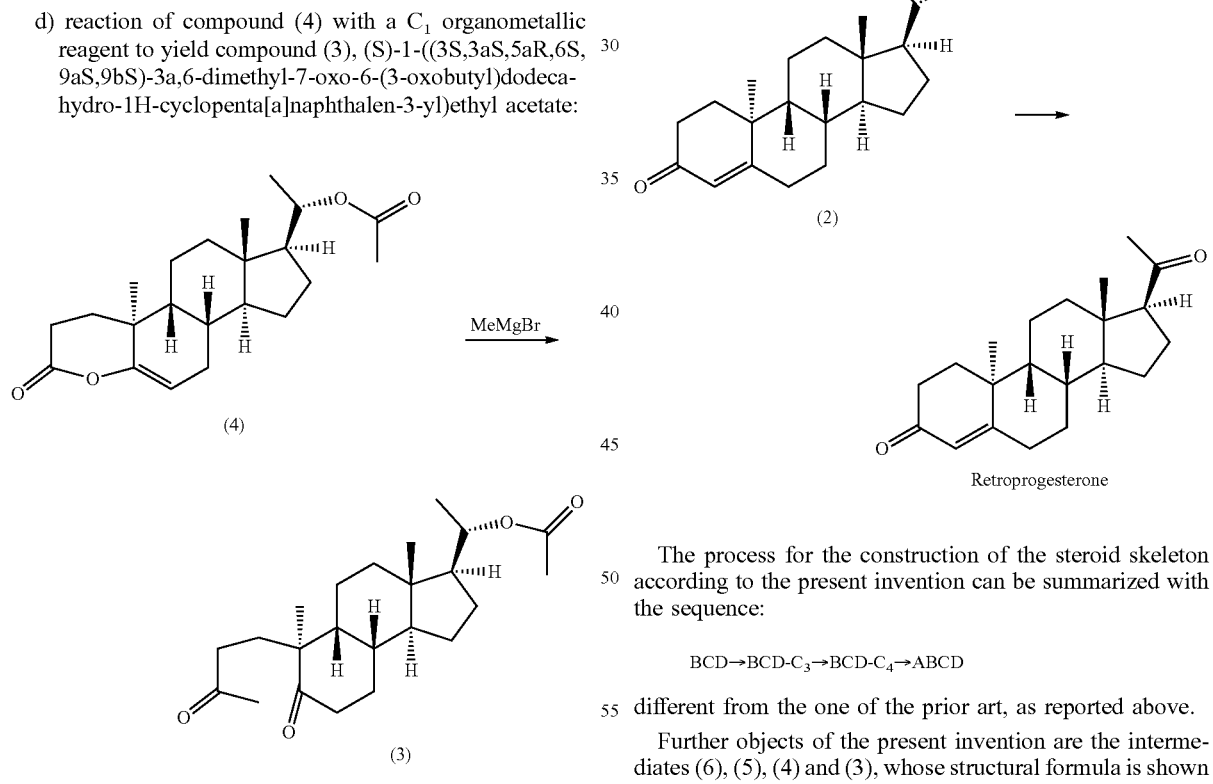

The process for the construction of the steroid skeleton according to the present invention can be summarized with the sequence:

BCD→BCD-C$_3$→BCD-C$_4$→ABCD different from the one of the prior art, as reported above.

Further objects of the present invention are the intermediates (6), (5), (4) and (3), whose structural formula is shown in the reaction sequence illustrated above.

DETAILED DESCRIPTION OF THE INVENTION

In the present description and in the claims, in the case of a discrepancy between the name of a compound and the structural formula reported for the same, the latter must be considered correct.

The starting material for the process of the invention is compound (7),

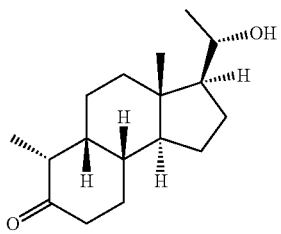

(7)

obtainable by hydrogenation of the following unsaturated precursor at atmospheric pressure and room temperature:

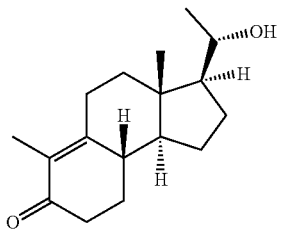

using rhodium on alumina as a catalyst in acidic alcoholic solution.

The reaction of step a) is carried out in a solvent selected from $C_1$-$C_{10}$ linear or branched aliphatic alcohols, either pure or in a mixture thereof, in the presence of an inorganic base and acrylonitrile. The preferred solvent is 2-methyl-2-butanol (also known in the field as tert-amyl alcohol).

The reaction temperature is between 25° C. and the boiling point of the reaction mixture, preferably between 45 and 75° C.

The base used is selected from sodium hydroxide, potassium hydroxide, and lithium hydroxide; the preferred base is sodium hydroxide.

The reaction time is between 4 and 24 hours, preferably 16 hours.

The amount by moles of acrylonitrile used is between 1 and 5 moles, preferably between 2 and 4 moles per mole of starting compound (7). Acrylonitrile may be added in portions during the reaction or, preferably, in a single addition.

The reaction of step b) is carried out in a basic aqueous solution in the presence of a reagent that favors phase mixing (phase transfer reagent).

The reaction temperature is between 50° C. and the boiling point of the reaction solution; it is preferable to work at the boiling point.

The base used is selected from sodium hydroxide, potassium hydroxide, and lithium hydroxide; the preferred base is sodium hydroxide.

A useful reagent to favor phase mixing (phase transfer reagent) is a quaternary ammonium salt, preferably benzyltrimethylammonium hydroxide (also known as Triton B).

The reaction of step c) is carried out in acetic anhydride, at a temperature between 100° C. and the boiling temperature of the reaction mixture, until disappearance of intermediate (5).

Acetic anhydride ($Ac_2O$) has the double role of solvent and reagent.

The reaction time is usually between 60 and 120 minutes, typically of about 90 minutes.

A base selected from sodium or potassium acetate (preferably sodium acetate) is then added to the reaction mixture, and it is refluxed for a time of between 60 and 120 minutes, preferably 90 minutes.

The reaction of step d) is carried out at a temperature of between −50° C. and −20° C., preferably between −35° C. and −25° C., in a solvent inert to the reaction conditions.

The solvent is selected from diethyl ether, isopropyl ether, dibutyl ether, tetrahydrofuran, methyltetrahydrofuran, dioxane, methyl tert-butyl ether, and toluene, either pure or in a mixture thereof. Preferably tetrahydrofuran is used, pure or in a mixture with a second solvent.

As a $C_1$ organometallic reagent, methylmagnesium chloride, methylmagnesium bromide, or methylmagnesium iodide may be used, dissolved in an organic solvent inert to the reaction conditions; preferably methylmagnesium bromide in tetrahydrofuran is used.

Between 1.5 and 5 moles of $C_1$ organometallic reagent are used per mole of intermediate (4), preferably between 3 and 4 moles.

The reaction of step e) is carried out in a solvent selected from methanol, ethanol, iso-propanol, tert-butanol, n-butanol, cyclohexanol, ethylene glycol, dioxane, tetrahydrofuran, methyltetrahydrofuran, either pure or as a mixture thereof, that may be used anhydrous or in the presence of water.

As a strong base, lithium, sodium, or potassium hydroxides, or lithium, sodium, potassium, or cesium carbonates may be used.

The preferred solvent/base combination for carrying out the reaction of step e) is methanol and sodium hydroxide.

The reaction temperature is between 40° C. and the boiling point of the reaction mixture, and preferably between 60° C. and said boiling temperature.

The reaction of step f) is carried out in water or a solvent lacking oxidizable functional groups, such as: esters (for example, ethyl acetate or isopropyl acetate); ketones (for example, acetone, methyl isobutyl ketone, or cyclohexanone); aliphatic or aromatic hydrocarbons (for example, heptane, toluene, or cyclohexane); and halogenated solvents (such as, methylene chloride or chloroform); these solvents can be used either pure or as a mixture thereof.

Compounds of chromium (VI); dimethylsulfoxide in the presence of an activator, such as for example the pyridine-$SO_3$ complex, or N-chlorosuccinimide (NCS; in this latter case the reaction is also known as Swern oxidation); aluminium or magnesium alkoxides according to the conditions known as the Oppenauer oxidation; periodinanes, such as triacetoxyperiodinane, 1,1,1-triacetoxy-1,1-dihydro-1,2-benziodoxol-3(1H)-one known as the Dess-Martin periodinane, o-iodoxybenzoic acid (known as IBX) and stabilized o-iodoxybenzoic acid (known as SIBX), can be used as oxidants.

The retroprogesterone so obtained can be used as an intermediate in the preparation of other steroids having pharmacological activity, such as for example Dydrogesterone, following the indications reported in the literature, for example in 79 (1960) Recueil 771-783.

The invention will be further illustrated by the following examples, which are reported only for illustrative purposes and are not to be considered as limiting the same.

The reagents used in the examples are commonly available commercially, and are used without further purification being needed.

Methods and Experimental Conditions

NMR:

Spectrometer: NMR JEOL 400 YH (400 MHz);

Tubes: NMR Aldrich® ColorSpec®;

Software: JEOL Delta v5.1.1;

Spectra recorded in deuterated chloroform supplied by Sigma-Aldrich: Chloroform-d, D 99.8% atomic, containing 0.1% (v/v) tetramethylsilane (TMS) as an internal standard; and chloroform-d, "100%", D 99.96% atomic, containing 0.03% (v/v) TMS.

MS:

HPLC-mass system: AB Sciex API 2000 LC/MS/MS;

Samples directly injected and chemically ionized (CI) with formic acid.

DSC:

Instrument: Perkin Elmer mod. Diamond;

Capsule: Perkin Elmer Standard aluminium and cover, cod. 02190041;

Scan speed: 10° C./min;

Temperature range: From 20° C. to 200° C.

IR:

Spectrometer: Thermo Scientific Nicolet 6700;

FT-IR spectra recorded in KBr (solids) and in smart-iTR-diffused reflectance (ATR);

Potassium bromide Sigma-Aldrich Cod. 221864 (for IR analysis).

HPLC:

Chromatographic system: Agilent model 1200

UV Detector MODEL 1260 DAD VL, and laser detector 1290 Infinity ELSD

TLC:

MERCK: TLC silica gel 60 $F_{254}$ Aluminium sheets 20×20 cm cod. 1.0554.0001.

HPTLC:

MERCK: HPTLC silica gel 60 with concentration zone 10×2.5 cm, cod. 1.13727.0001.

TLC-RP:

MERCK: TLC silica gel 60 RP-18 S, cod. 1.15685.0001.

TLC Stains:

Acidic solution of cerium phosphomolybdate;

Preparation: 25 g of phosphomolybdic acid hydrate (Aldrich P7390), 10 g cerium (IV) sulfate hydrate (Aldrich 31606) and 600 mL of water are stirred until dissolution with 60 mL 95-98% sulfuric acid (Aldrich 258105); this is brought to a final volume of 1000 mL with water; the plate is dipped in the solution, then heated until a blue color is observed.

UV lamp at 254 and 366 nm.

XRD:

Bruker $D_2$ Phaser;

X-ray source: copper tube with X=1.54184 [A] powered with 30 kV and 10 mA;

Scan speed: 0.02° 2θ/second;

Scan range from 5° to 35° 2θ;

Analysis time: 1478 steps in 1704 seconds;

Rotation 10° [1°/min];

Detector SSD160 (ID mode) with a PSD (Position Sensitive Detector) detector aperture of 4.60.

Example 1

This example relates to step a) of the process of the invention.

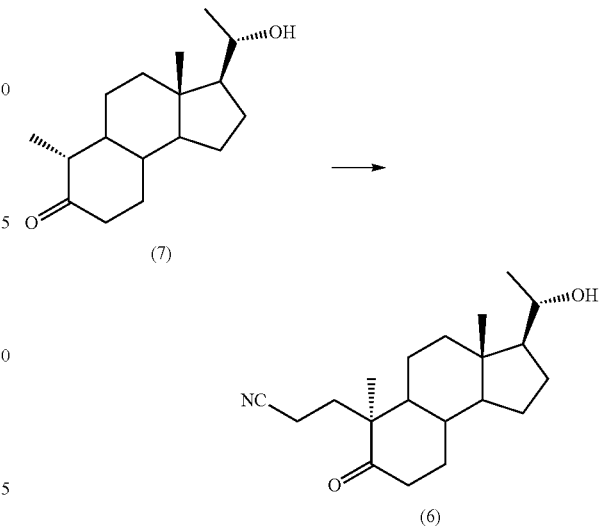

180 mg of sodium hydroxide and 180 mL of tert-amyl alcohol are loaded into a 1 L round-bottomed flask, under a nitrogen flow. The reaction is stirred at 50° C. for 60 minutes.

A solution of intermediate (7) (12 g dissolved in 120 mL tert-amyl alcohol) is added to it. This was stirred at 50° C. for 60 minutes.

A solution of acrylonitrile (7.24 g in 108 mL of tert-amyl alcohol) is added dropwise over 30 minutes. This was stirred at 50° C. for 16 hours.

After TLC control (Eluent: 7/3 isopropyl acetate/heptane; plate: silica gel; stain: UV/cerium phosphomolybdate—Sample: Reaction mixture poured into acidic water and extracted with isopropyl acetate) the formation of the intermediate (6) compared to unreacted intermediate (7) is detected.

It is brought to 20-25° C., and 200 mL of water containing 0.25 mL of acetic acid is added, stirring it for 10 minutes. The pH is checked to be between 5 and 6.

The solvent is removed on the rotavapor at 45° C. under vacuum, and next the aqueous phase is extracted with isopropyl acetate (2×100 mL).

The combined organic layers are first washed with water (100 mL), then solvent is removed on the rotavapor at 45° C. under vacuum to obtain a brown oil (20.08 g) which is used as is in the next reaction.

A small portion of the brown oil is purified by chromatography on silica gel (Eluent: 50:50→40:60 heptane/isopropyl acetate) for analytical purposes. After removal of the solvent to constant weight, the residue obtained is analyzed.

The results of the analytical tests are in agreement with the structure identified in the text as intermediate (6): $M^+=317=C_{20}H_{31}NO_2$:

Ms(CI): $M^++1=318$; $M^++1-H_2O=300$; $M^++1-2H_2O=282$; $M^++1-H_2O-CH_3CHO=256$

Regarding the starting material (7), $M^+=264=C_{17}H_{28}O_2$, the analytical tests provide results in agreement with the structure:

Ms(CI): $M^++1=265$; $M^++1-H_2O=247$; $M^++1-2H_2O=229$

Example 2

This example relates to step b) of the process of the invention.

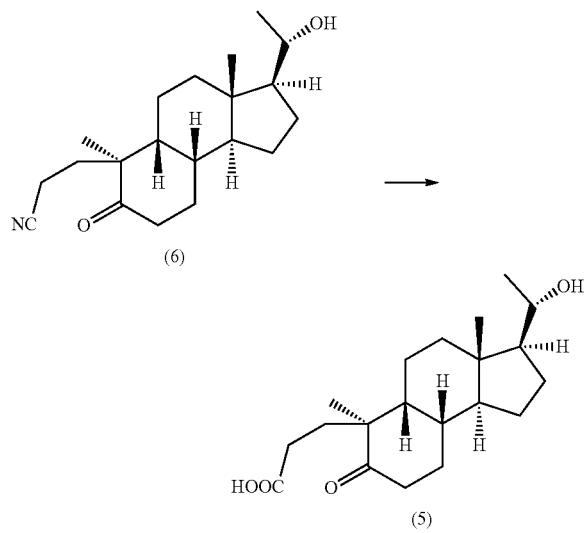

The intermediate (6) obtained from the previous reaction (19.9 g) is stirred with 200 mL of a 4M sodium hydroxide aqueous solution and 5 mL of Triton B, 40% in water, bringing the mixture to reflux.

After 6 h, the reaction progress is checked by TLC (Eluent: 7/3 Isopropyl acetate/heptane with 0.1% acetic acid; plate: silica gel; stain: UV/cerium phosphomolybdate—Sample: Reaction mixture in acidic water, extracted with MTBE): reaction complete.

The reaction is cooled to 20-25° C. and extracted with 250 mL of MTBE (organic phase A).

The organic phase A is washed with 100 mL of 2 M aqueous NaOH solution.

The basic organic phases are combined, cooled to 10-15° C., and acidified to pH=2 with 3 M HCl, keeping T<30° C.

The acidic aqueous phase is extracted with 400 mL of MTBE (organic phase B).

The organic phase B is washed with water, and then with a saturated aqueous NaCl solution.

The solvent is removed on the rotavapor at 45° C. under vacuum, obtaining 19.2 g of yellow oil (intermediate 5).

The organic phase A is washed with water, and then with a saturated aqueous NaCl solution.

After removal of the solvent using a rotavapor, 2 g of yellow oil is obtained, which is found to be mostly intermediate (6).

A small portion of intermediate (5) is purified by chromatography on silica gel (80:20 ethyl acetate/heptane+0.1% acetic acid) for analytical purposes. After removal of the solvent to constant weight, the residue is analyzed.

The results of the analytical tests carried out are in agreement with the structure identified in the text as intermediate (5): $M^+=336=C_{20}H_{32}O_4$:

Ms(CI): $M^++1=337$; $M^++1-H_2O=319$; $M^++1-2H_2O=301$; $M^++1-H_2O-CH_3CHO=275$.

Example 3

This example refers to step c) of the process of the invention.

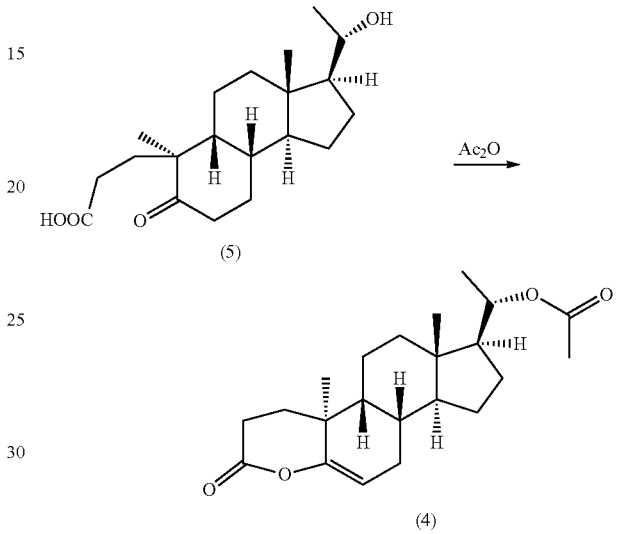

Intermediate (5), obtained as described in the previous example (18.9 g), is suspended in 80 mL of acetic anhydride, to obtain an opalescent solution; the solution is filtered through cotton, and the filter washed with a further 300 mL of acetic anhydride.

The solution is brought to reflux for 90 minutes (T=135° C.) checking the progress of the reaction by TLC: the starting material disappears and the formation of two distinct products is detected (Sample: Reaction mixture in water, extracted with MTBE; Eluent: 7/3 isopropyl acetate/heptane 7/3 with 0.1% acetic acid; plate: silica gel; stain: UV/cerium phosphomolybdate). 9.7 g of dry sodium acetate are added, and the mixture is refluxed for additional 90'.

The mixture is cooled to about 40° C., and acetic anhydride is removed under reduced pressure.

The residue is dissolved in 300 mL of MTBE, washed with 200 mL of saturated aqueous $NaHCO_3$ solution, and the aqueous phase is extracted again with 200 mL of MTBE.

The combined organic phases are washed with 200 mL of saturated aqueous NaCl solution. The organic solvent is removed on the rotavapor under vacuum at 45° C., to obtain a brown oil (18.6 g) containing intermediate (4).

The brown oil is purified by medium pressure chromatography on silica gel (Eluent: 85:15 heptane/ethyl acetate) to obtain, after drying to constant weight, 8.2 g of intermediate (4) as a white solid.

The results of the analytical tests carried out are in agreement with the structure identified in the text as intermediate (4): $M^+=360=C_{22}H_{32}O_4$:

Ms(CI): $M^++1=361$; $M^++1-CH_3COOH=301$; $M^++1-CH_3COOH-H_2O=283$.

Example 4

This example relates to step d) of the process of the invention.

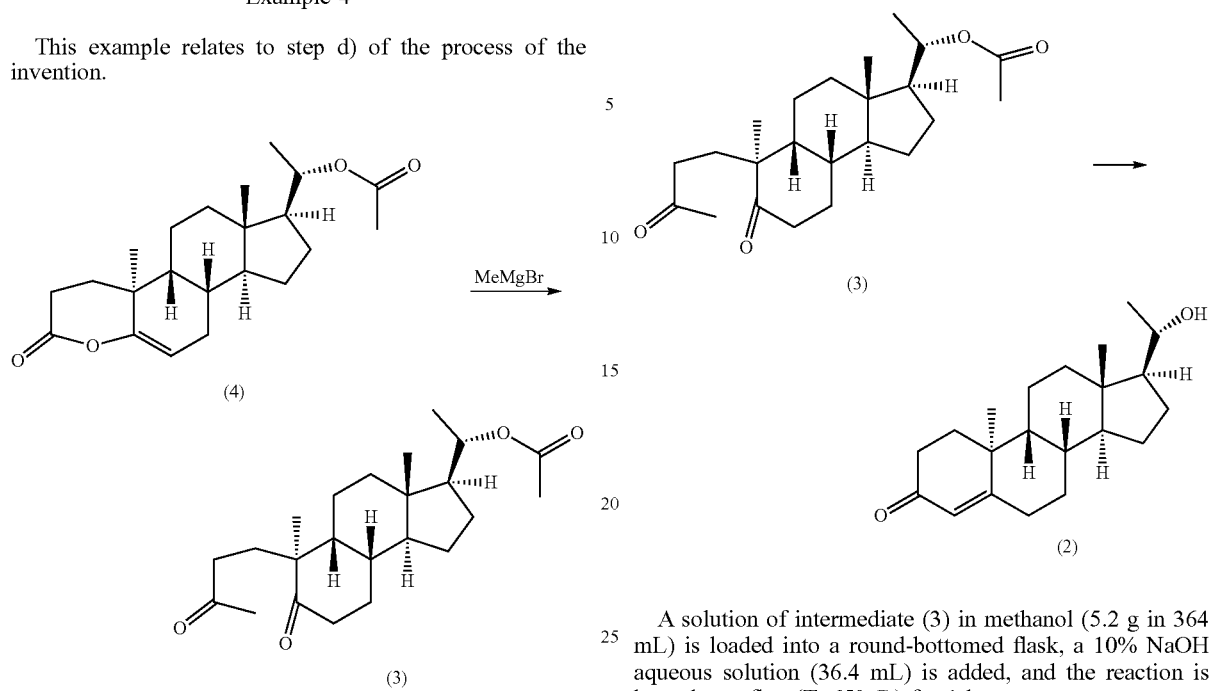

5.5 g of intermediate (4), obtained as described in the previous example and dissolved in THF (66 mL), are loaded into a round-bottomed flask.

It is cooled to a temperature between −30 and −35° C., and a solution of 1M methylmagnesium bromide, $CH_3MgBr$, prepared by diluting 18.4 mL of a commercial solution of 3M methylmagnesium bromide with 36.8 mL of THF, is added while keeping the temperature lower than −25° C.

At the end of addition, the temperature is maintained at T=−30±5° C. for 30 minutes.

The reaction progress is monitored by TLC (Sample: Reaction mixture in aqueous ammonium chloride solution, extracted with MTBE—Eluent: 7/3 isopropyl acetate/heptane; plate: silica gel; stain: UV/cerium phosphomolybdate): reaction complete, intermediate (4) disappeared.

It is poured onto a 15% $NH_4Cl$ aqueous solution (200 mL), pre-cooled to 0-5° C., while keeping T<10° C. and stirring for 10 minutes. 200 mL of MTBE is added and kept stirring for 1 h at T=25° C.

The phases are separated, and the aqueous phase is re-extracted with 100 mL MTBE.

The combined organic phases are washed with 250 mL water. The organic phases are evaporated under vacuum at 45° C., to obtain 5.3 g of intermediate (3).

A small portion of intermediate (3) is purified by chromatography on silica gel (Eluent: 70/30 heptane/ethyl acetate) for analytical purposes. After removal of the solvent to constant weight, the residue obtained is analyzed.

The results of the analytical tests carried out are in agreement with the structure identified in the text as intermediate (3): $M^+=376=C_{23}H_{36}O_4$:

Ms(CI)   $M^++1=377$;   $M^++1—H_2O=359$;   $M^++1—2H_2O=341$;   $M^++1—CH_3COOH=317$;   $M^++1—CH_3COOH—H_2O=299$; $M^++1—CH_3COOH—2H_2O=281$.

Example 5

This example relates to step e) of the process of the invention.

A solution of intermediate (3) in methanol (5.2 g in 364 mL) is loaded into a round-bottomed flask, a 10% NaOH aqueous solution (36.4 mL) is added, and the reaction is heated to reflux (T=65° C.) for 1 h.

The reaction progress is monitored by TLC: intermediate (3) disappeared. (Sample: Reaction mixture diluted in methanol; Eluent: 7/3 isopropyl acetate/heptane; plate: silica gel; stain: UV/cerium phosphomolybdate).

The methanol is removed on the rotavapor at 45° C. under vacuum, and the residue is taken up with 320 mL of 10% aqueous NaOH solution. This is extracted with MTBE (320 mL+150 mL). The combined organic phases are washed with saturated aqueous NaCl solution.

The organic solvent is removed under vacuum at 45° C., to obtain 3.9 g of solid (intermediate 2).

A small portion of intermediate (2) is purified by chromatography on silica gel (Eluent 85:15 heptane/ethyl acetate) for analytical purposes. After removal of the solvent to constant weight, the residue obtained is analyzed.

The results of the analytical tests carried out are in agreement with the structure identified in the text as intermediate (2): $M^+=316=C_{21}H_{32}O_2$:

Ms(CI)   $M^++1=317$;   $M^++1—H_2O=299$;   $M^++1—2H_2O=281$.

Example 6

This example relates to step e) of the process of the invention.

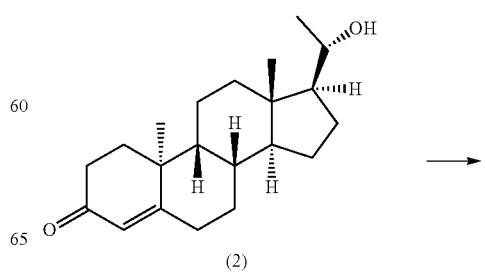

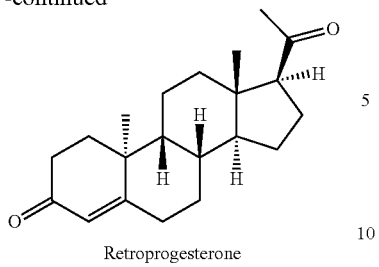

Retroprogesterone

In a round-bottomed flask, 3.8 g of intermediate (2) obtained as described in the previous example is dissolved in isopropyl acetate, while heating to about 60° C.

SIBX (8.96 g) is added, and the reaction brought to reflux (88° C.) for 6 h. TLC: complete (Sample: Reaction mixture treated with an aqueous $NaHCO_3$ solution and extracted with isopropyl acetate. Eluent: 7/3 isopropyl acetate/heptane; plate: silica gel; stain: UV/cerium phosphomolybdate).

The reaction mixture is cooled to 25° C. and filtered through Celite, washing with 20 mL of isopropyl acetate.

50 mL of saturated aqueous $NaHCO_3$ solution is added, and the mixture stirred for 10 minutes. The phases are separated, and 50 mL of a 15% sodium metabisulfite aqueous solution are added to the organic phase, while keeping under stirring for 10 minutes.

The phases are separated, and the organic phase is washed with 50 mL of a saturated aqueous NaCl solution.

The phases are separated, and the solvent is removed on the rotavapor at 45° C. under vacuum, to obtain 3.6 g of retroprogesterone (yellow solid).

A portion of retroprogesterone is purified by chromatography on silica gel using a gradient of heptane/ethyl acetate from 7/3 to 6/4.

The results of the analytical tests carried out on the sample dried to constant weight are in agreement with the structure of retroprogesterone: $C_{21}H_{30}O_2=314$.

Ms(CI): $M^++1=315$; $M^++1—H_2O=297$ FT-IR(KBr): 1,693 $cm^{-1}$; 1,664 $cm^{-1}$; 1,610 $cm^{-1}$.

$^1$H-NMR ($CDCl_3$): 5.73 ppm, s, 1H; 2.14 ppm, s 3H; 1.37 ppm, s, 3H; 0.68 ppm, s, 3H.

$^{13}$C-NMR ($CDCl_3$): 209.2; 199.5; 172.2; 123.9; 64.7; 47.7; 45.5; 44.3; 39.9; 37.9; 37.4; 35.2; 33.7; 31.5; 29.1; 28.9; 24.9; 22.9; 22.3; 22.2; 12.7 (ppm).

The invention claimed is:

1. Process for the synthesis of retroprogesterone, comprising the following steps:
    a) reaction of compound (7), (3S,3aS,5aR,6R,9aR,9bS)-3-((S)-1-hydroxyethyl)-3a,6-dimethyldodecahydro-7H-cyclopenta[a]naphthalen-7-one, with acrylonitrile to yield compound (6), 3-((3S,3aS,5aR,6S,9aS,9bS)-3-((S)-1-hydroxyethyl)-3a,6-dimethyl-7-oxododecahydro-1H-cyclopenta[a]naphthalen-6-yl)propanenitrile:

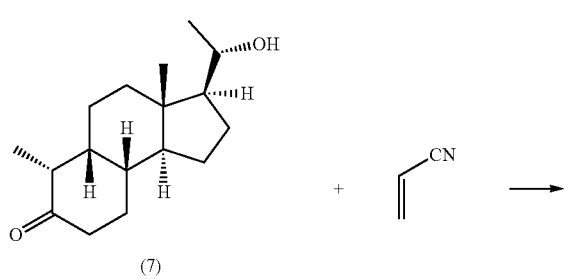

b) reaction of compound (6) with a strong base to yield compound (5), 3-((3S,3aS,5aR,6S,9aS,9bS)-3-((S)-1-hydroxyethyl)-3a,6-dimethyl-7-oxododecahydro-1H-cyclopenta[a]naphthalen-6-yl)propanoic acid:

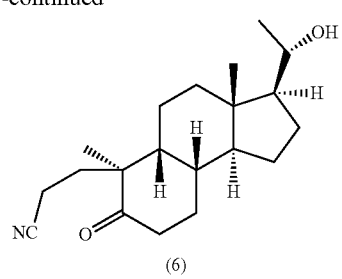

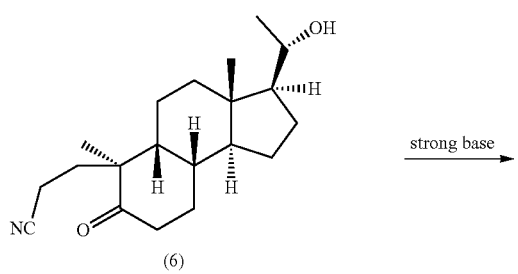

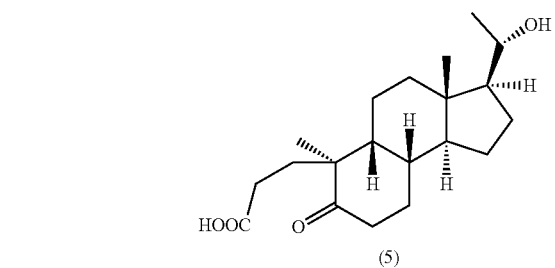

c) reaction of compound (5) with acetic anhydride, $Ac_2O$, to yield compound (4), (S)-1-((4aS,4bR,6aS,7S,9aS,9bS)-4a,6a-dimethyl-2-oxo-2,3,4,4a,4b,5,6,6a,7,8,9,9a,9b,10-tetradecahydroindeno[5,4-f]chromen-7-yl)ethyl acetate:

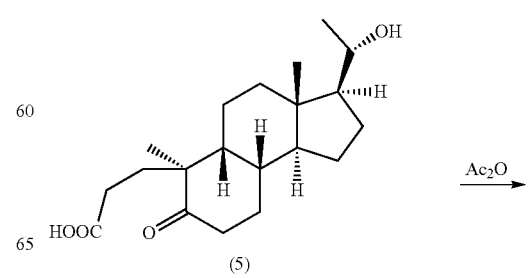

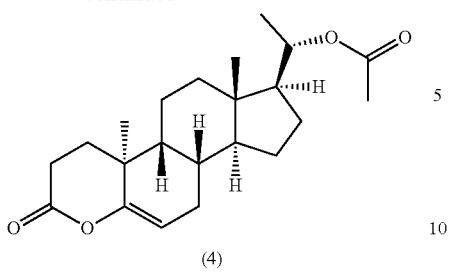

(4)

d) reaction of compound (4) with a C₁ organometallic reagent to yield compound (3), (S)-1-((3S,3aS,5aR,6S,9aS,9bS)-3a,6-dimethyl-7-oxo-6-(3-oxobutyl)dodecahydro-1H-cyclopenta[a]naphthalen-3-yl)ethyl acetate:

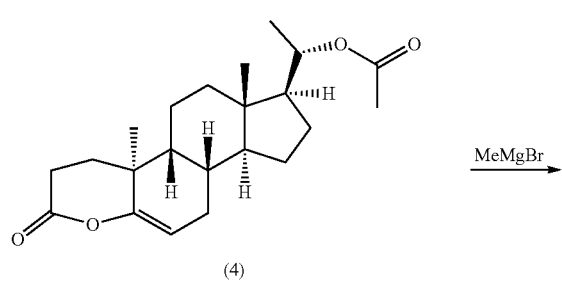

wherein by "C₁ organometallic reagent" is meant an organometallic compound in which the organic moiety comprises only one carbon atom;

e) reaction of compound (3) with a strong base to yield compound (2), (8S,9R,10S,13S,14S,17S)-17-((S)-1-hydroxyethyl)-10,13-dimethyl-1,2,6,7,8,9,10,11,12,13,14,15,16,17-tetradecahydro-3H-cyclopenta[a]phenanthren-3-one:

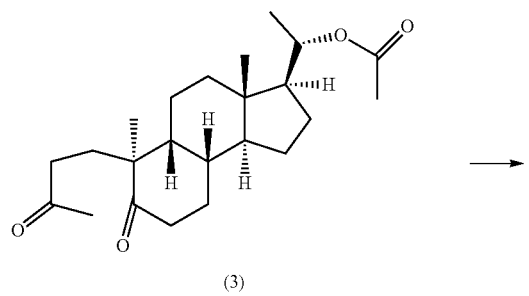

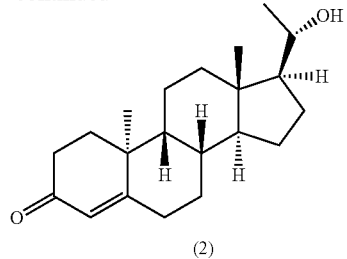

(2)

f) oxidation of intermediate (2) to obtain retroprogesterone:

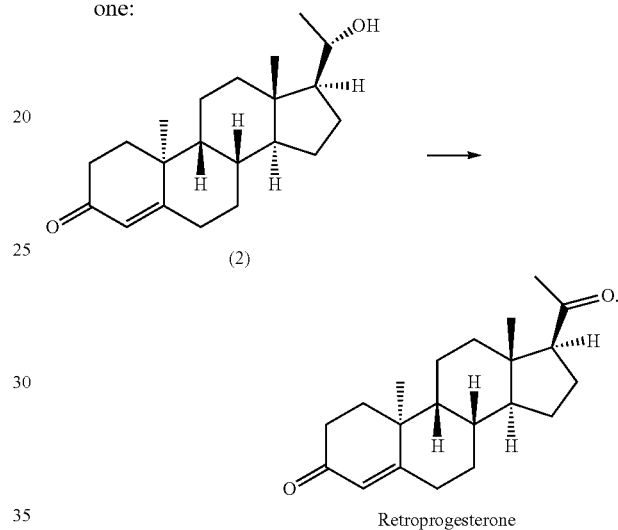

2. 3-((3S,3aS,5aR,6S,9aS,9bS)-3-((S)-1-hydroxyethyl)-3a,6-dimethyl-7-oxododecahydro-1H-cyclopenta[a]naphthalen-6-yl)propanenitrile, compound of formula (6): (6)

3. 3-((3S,3aS,5aR,6S,9aS,9bS)-3-((S)-1-hydroxyethyl)-3a,6-dimethyl-7-oxododecahydro-1H-cyclopenta[a]naphthalen-6-yl)propanoic acid, compound of formula (5): (5)

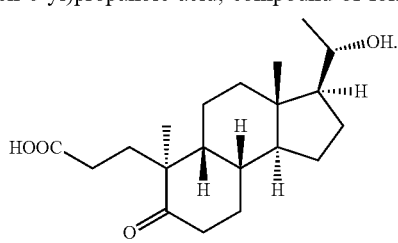

4. (S)-1-((4aS,4bR,6aS,7S,9aS,9bS)-4a,6a-dimethyl-2-oxo-2,3,4,4a,4b,5,6,6a,7,8,9,9a,9b,10-tetradecahydroindeno[5,4-f]chromen-7-yl)ethyl acetate, compound of formula (4):
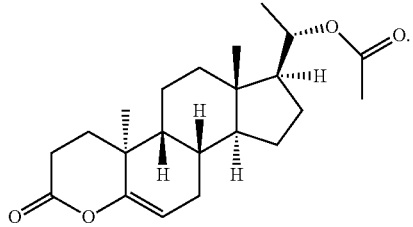
(4)
5. (S)-1-((3S,3aS,5aR,6S,9aS,9bS)-3a,6-dimethyl-7-oxo-6-(3-oxobutyl)dodecahydro-1H-cyclopenta[a]naphthalen-3-yl)ethyl acetate, compound of formula (3):
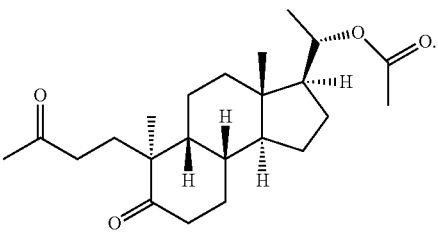
(3)
* * * * *